(12) United States Patent
Berndtsson

(10) Patent No.: US 6,387,328 B1
(45) Date of Patent: May 14, 2002

(54) DISPOSABLE SAMPLING DEVICE FOR PARTICLE COUNTING APPARATUS

(75) Inventor: Ingemar Berndtsson, Sollentuna (SE)

(73) Assignee: Boule Medical AB, Stockholm (SE)

( * ) Notice: Subject to any disclaimer, the term of this patent is extended or adjusted under 35 U.S.C. 154(b) by 0 days.

(21) Appl. No.: 09/446,918

(22) PCT Filed: May 28, 1998

(86) PCT No.: PCT/SE98/01033
§ 371 Date: Dec. 30, 1999
§ 102(e) Date: Dec. 30, 1999

(87) PCT Pub. No.: WO99/01742
PCT Pub. Date: Jan. 14, 1999

(30) Foreign Application Priority Data

Jul. 1, 1997 (SE) .............................. 9702541

(51) Int. Cl.$^7$ .............................. G01N 33/00
(52) U.S. Cl. .............................. 422/73; 422/81; 422/100; 422/103; 436/52; 436/179; 436/180; 73/61.71; 73/864.21; 73/864.81; 73/864.83
(58) Field of Search .............................. 422/68.1, 73, 81, 422/100, 103; 436/52, 63, 179, 180; 435/287.1, 287.3; 73/61.71, 864.21, 864.22, 864.81, 864.83, 864.87, 865.5

(56) References Cited

U.S. PATENT DOCUMENTS

| | | | | |
|---|---|---|---|---|
| 4,090,129 A | * | 5/1978 | Gear | 324/71.1 |
| 4,631,483 A | * | 12/1986 | Proni et al. | 324/71.4 |
| 4,729,876 A | * | 3/1988 | Hennessy et al. | 422/103 |
| 5,007,296 A | * | 4/1991 | Hukuhara | 73/864.87 |
| 6,098,471 A | * | 8/2000 | Berndsson et al. | 73/864.87 |

FOREIGN PATENT DOCUMENTS

| | | | |
|---|---|---|---|
| EP | 311588 | * | 4/1989 |
| WO | 95 17252 | | 6/1995 |
| WO | 95 25269 | | 9/1995 |
| WO | 98/22797 | * | 5/1998 |

* cited by examiner

*Primary Examiner*—Maureen M. Wallenhorst

(57) ABSTRACT

A disposable sampling device for an apparatus for counting particles contained in a liquid, including a solid block-shaped housing connectable in a defined position to the apparatus. The housing has a member for introducing a sample therein, a device for metering a defined volume of the sample, and a chamber for containing a defined volume (V) of a diluting liquid. A diluting chamber is provided together with a device for simultaneously directing the defined volume of a sample and the defined volume of diluting liquid to the diluting chamber for obtaining therein a diluted sample. A device is provided for directing at least a portion of the diluted sample past a particle detecting member, and a signal transmitting member connects the particle detecting member and terminal member located at an outer boundary of the housing in a position corresponding to a location of a terminal member of the apparatus when the housing is connected thereto in the defined position.

11 Claims, 7 Drawing Sheets

DISPOSABLE SAMPLING DEVICE FOR PARTICLE COUNTING APPARATUS

This application is the national phase under 35 U.S.C. §371 of PCT International Application No. PCT/SE98/01033 which has an International filing date of May 29, 1998, which designated the United States of America.

BACKGROUND OF THE INVENTION

1. Field of the Invention

The present invention concerns a disposable sampling device for an apparatus for counting particles contained in a liquid, such as blood cells in a blood sample and yeast fungus in wort, according to the preamble of claim 1.

2. Description of Background Art

It is known in the state of art to count blood cells by causing a volume of diluted blood sample to pass a so-called capillary, i.e., an extremely small hole, generally in a ruby, the hole having a diameter considerably larger than the size of a blood cell, typically 80 µm. A voltage is applied over the capillary, and, when a blood cell passes through the hole, the electrical resistance changes. This is because the cells can be regarded as insulators. Each change in resistance can be detected by suitable electronic equipment, and the sum of all changes detected corresponds to the number of blood cells having passed through the capillary. In order to obtain the concentration of cells in the original sample, the concentration of cells in the diluted sample is multiplied by the dilution factor, typically 1:40000 when counting of red blood cells (RBC) is concerned. It is obvious, that measuring of sample volumes and dilution liquid volumes must be performed in an accurate and repeatable way such that not only a correct degree of dilution can always be guaranteed but also a thorough and uniform mixing of the two volumes is ensured.

SUMMARY AND OBJECTS OF THE INVENTION

In a typical state of art apparatus, used for counting blood cells, a syringe is employed for providing a defined volume (typically 5 ml) of diluting liquid, and this volume is displaced through a conduit to a measuring chamber. On its way to the measuring chamber, the diluting liquid brings with it a defined volume (typically 25 µl) of blood sample previously introduced into the conduit. The blood sample mixes with and is diluted by the diluting liquid in the measuring chamber, which is, thus, also a dilution or mixing chamber, and a defined fraction of the diluted sample is further displaced through a capillary located in a wall of the measuring chamber, or, in a transducer located within the measuring chamber. In this state of art device, all components, except a vessel containing a blood sample, are permanently included in an apparatus containing also electronic equipment needed for counting particles and performing calculations necessary for obtaining resulting concentration values. Consequently, all components contacted by blood must be thoroughly cleaned after each counting procedure, such as by flushing with a suitable rinsing liquid. Also, this device is expensive and rather cumbersome, and, therefore, does not lend itself to use outside more well-equipped and established medical institutions, such as hospitals, public health centres and larger private surgeries.

There is a need, thus, to provide a relatively cheap and simple device for sampling, e.g. a blood sample or a wort sample, for use with a more stationary particle counting apparatus. The sampling device shall be useful outside medical institutions of the general kind mentioned—as regards blood sampling—as well as in breweries—as regards wort sampling. It shall also be easy to handle even by relatively unskilled personnel, and all its components contacted by a sample shall be contained within a disposable housing. The housing shall not contain expensive components, such as electronic equipment for the actual particle counting and evaluating purposes.

The present invention has as its object to provide a sampling device that fulfills the above need.

To achieve this, the present invention suggests a disposable sampling device for an apparatus for counting particles contained in a liquid, comprising a solid block-shaped housing connectable in a defined position to said apparatus, said housing having therein means for introducing a sample into said housing; means for metering a defined volume of said sample; means containing a defined volume of a diluting liquid; means defining a diluting chamber; means for simultaneously directing said defined volume of said sample and said defined volume of said diluting liquid to said diluting chamber for obtaining therein a diluted sample; means for directing at least a portion of said diluted sample past particle detecting means; signal transmitting means connecting said particle detecting means and terminal means located at an outer boundary of said housing in a position corresponding to a location of terminal means of said apparatus when said housing is connected thereto in said defined position.

BRIEF DESCRIPTION OF THE DRAWINGS

Embodiments of the present invention will be described hereinafter, reference being made to the annexed drawings, wherein.

DETAILED DESCRIPTION OF THE PREFERRED EMBODIMENT

Figure 1:
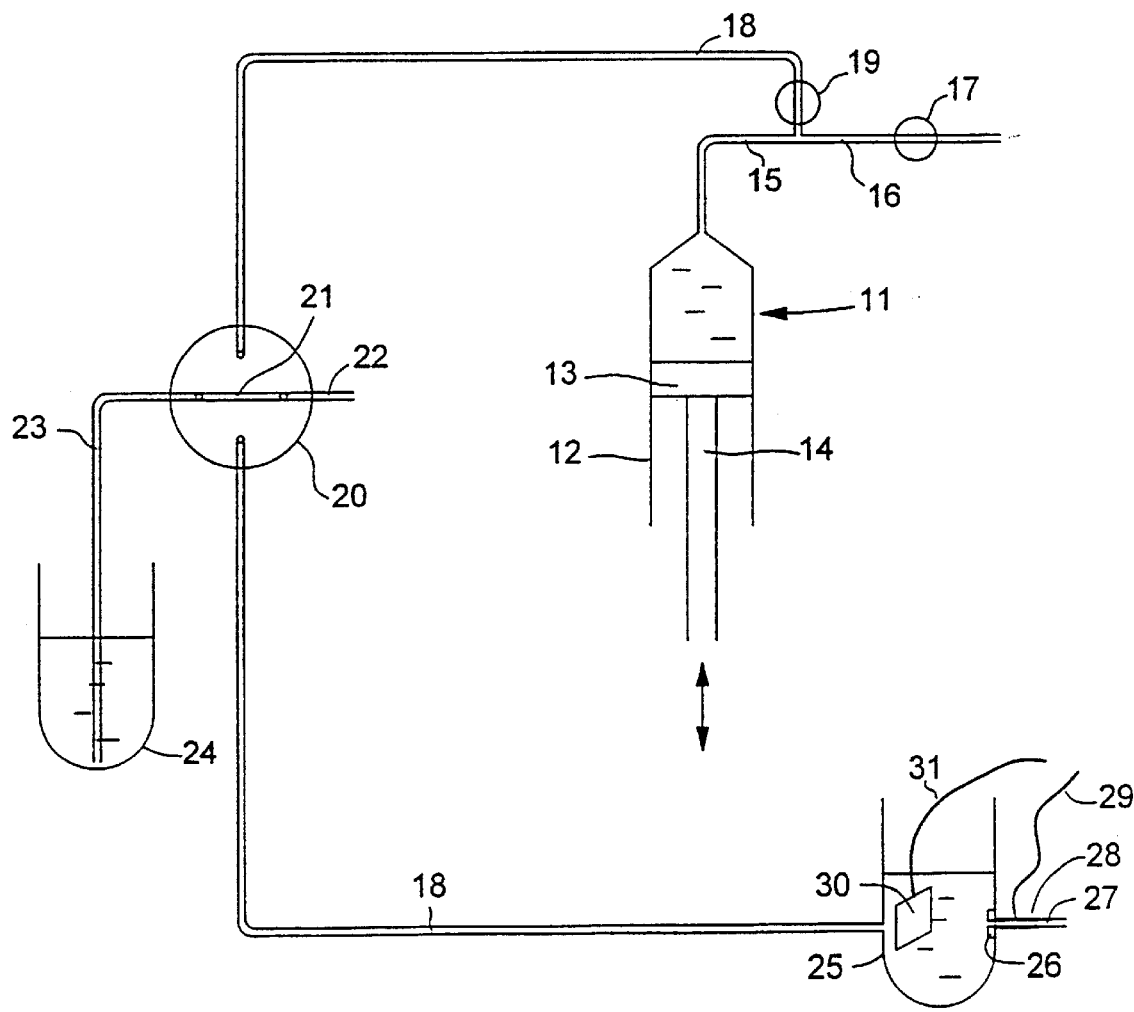
FIG. 1 is a schematic view showing a state of the art apparatus.
Figure 2:
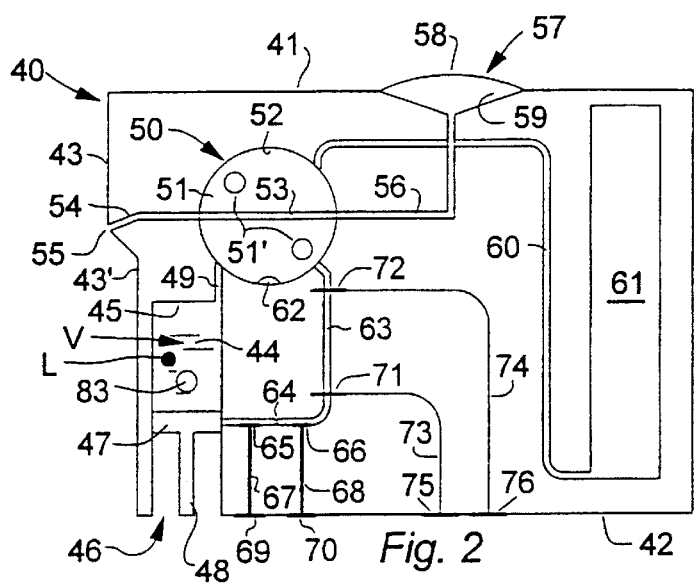
FIGS. 2–9 show schematic sections through a first embodiment of a device according to the present invention in various steps of its measuring cycle.

In the state of art arrangement according to FIG. 1, 11 is a syringe including a cylinder 12 and a piston 13 axially movable within the cylinder by means of a piston rod 14 extending through one end of the cylinder, that may be an open end. The opposite end of the cylinder is closed and connected to a conduit 15. This conduit 15 in turn communicates with a supply conduit 16 for diluting liquid having a valve 17 therein, and a discharge conduit 18 having a valve 19 therein. In the conduit 18 there is also a turning valve 20, the non-shown rotatable valve body of which has a through channel 21 and is positionable in two different positions. In a first position (shown in FIG. 1), the through channel communicates with a conduit 22 leading to a non-shown pump, and a conduit 23 communicating with a vessel 24 containing a blood sample to be diluted. The blood sample in the vessel 24 may be diluted already to a certain extent.

The discharge conduit 18 ends in a mixing and measuring chamber 25. In a wall of the chamber 25 there is a capillary 26 and a discharge conduit 27 including a metallic portion 28 constituting an electrode connected to an electric wire 29. A further electrode 30 is located within the chamber 25 and is connected to an electric wire 31. A voltage may be applied across the capillary by connecting wire 29 to one pole and wire 31 to the other pole of a suitable electronic counting equipment.

Upon operation of the pump, blood sample is transported from the vessel 24 through the valve 20 so as to fill the through channel 21. In a second position of the valve body, the through channel communicates with the conduit 18. Since the through channel 21 contains an accurately defined volume, turning of the valve body to the second position will put this defined volume in communication with the conduit 18.

The function of the known device is as follows: The valve 17 is opened and the piston lowered to suck a defined volume of diluting liquid into the syringe. Thereafter, the valve 17 is closed and the valve 19 opened, and the piston 13 is raised thereby displacing diluting liquid through the conduit 18 through the valve 20, the valve body of which being positioned in its second position so that the defined volume of blood sample is brought by the diluting liquid to the mixing and measuring chamber 25 where the very small volume of blood sample is mixed with and diluted by the relatively large volume of diluting liquid. A defined portion of the mixed and diluted sample is brought through the capillary 26, and the blood cells are counted by the electronic counting equipment.

The embodiments of the disposable particle counting device of present invention to be described hereinafter with reference to FIGS. 2–9 (first embodiment) and FIGS. 10 and 11 (second embodiment) utilize some of the features of the prior art device described above, while others have been replaced by such more suitable for a disposable, self-contained product.

The device comprises a substantially block-shaped body 40 (see FIG. 12), preferably made of a transparent material, such as a moldable synthetic resin and having an upper wall 41, a bottom wall 42 and a front wall 43. In the body 40, there is provided a cylinder 44 having an upper end 45 and a lower end 46. A piston 47 is axially movable within the cylinder by means of a piston rod 48 accessible from outside the housing at the lower end 46 of the cylinder, the upper end 45 of which being connected to a channel 49 provided in the housing.

In the housing there is also provided a turning valve 50 having a valve body 51 rotatable within a cylindrical valve chamber 52. An actuating means, such as a diametrically extending slot or two diametrically opposed holes 51', is provided to rotate the valve body from outside the housing. A through channel 53 extends across the valve body which is positionable in two different positions.

In a first position (shown in FIGS. 2, 3, 4, 9, 10 and 11), the through channel communicates with an intake channel 54 in the housing opening in a sample receiving aperture 55 in the front wall 43 and a sucking channel 56 leading to a sucking means in the shape of a diaphragm pump 57 having a resilient diaphragm 58 covering a conical recess 59 in the upper wall 41.

In a second position (shown in FIGS. 5–8), the through channel 53 communicates with the channel 49 from the cylinder 44 and with a channel 60 leading to the bottom of a relatively large volume space 61 provided within the housing 40.

In the second position of the valve body, a bleeding recess 62 provided at the circumference of the valve body 51 communicates with a channel 63 opening in the cylinder 44.

In the channel 63 there is a capillary 64 and on either sides thereof an electrode 65, 66 connected to a respective conductor 67, 68 terminating in a respective terminal 69, 70. In the channel 63 there are also two detectors 71 and 72 having signal transmitting conductors 73, 74, respectively, terminating in respective terminals 75, 76 in the bottom wall 42. The detectors may, e.g., be optical detectors, and in such case the conductors 73, 74 are optical fibres. Also possible is that the detectors are capacity sensitive detectors, and in such case the conductors 73, 74 are electric coductors. In any case, the detectors are adapted to start and stop, respectively, particle counting.

When manufacturing a device according to the present invention, a volume V of the cylinder 44 is filled with a liquid L, such as a diluting liquid. The volume V is defined by the piston 47 in an axial position thereof where it covers the mouth of the channel 63.

Operation of the device will now be described with reference to blood sampling. Initially, the valve body and the piston occupy the positions shown in FIG. 2.

Figure 3:
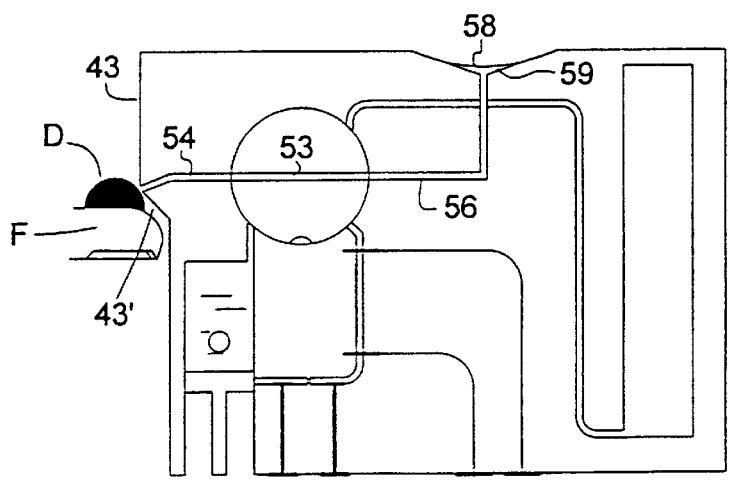

In FIG. 3 is shown that the diaphragm has been depressed, e.g. by a fingertip of an operator, so as to expel a volume of air contained under the diaphragm within the conical recess 59 through the sucking channel 56, the through channel 53 and the channel 54 to the open air. It is also shown how a punctured fingertip F having a drop D of blood on it is approached to the front wall 43 of the device where the wall exhibits a stepped recess 43' so as to locate the drop in a proper position in relation to the mouth of the channel 54. Next, the diaphragm is released and allowed to regain its original position as shown in FIG. 4.

Figure 4:
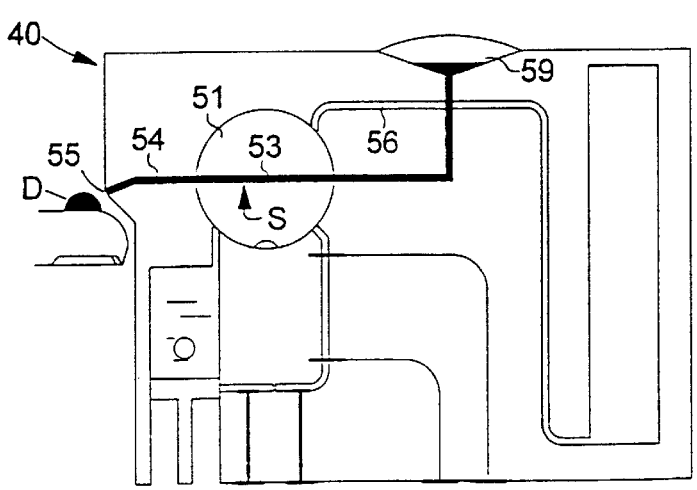

In FIG. 4 is shown how a sample S of blood has been sucked from the drop D to fill the channels 54, 53 and 56 as well as a portion of the conical recess 59. As initially stated, it is important to make sure that the through channel is properly filled, since it contains an accurately defined volume. When the housing 40 and the valve body 51 are made of a transparent material, it is easy to determine whether the through channel 53 is filled or not. When it is established that the sample taken is satisfactory, the aperture 55 is closed, for instance by an adhesive tape or the like. This is the last step that is ordinary performed by a sampling person in the field. The following steps are ordinarily performed by a-centrally located particle counting apparatus.

Figure 5:
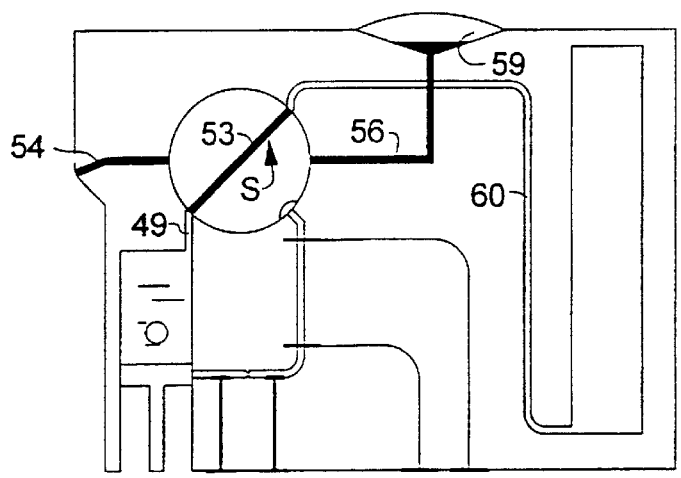

In the first following step, the valve body 51 is rotated to its second position as shown in FIG. 5 so as to separate the volume of sample contained within the through channel from the remainder thereof contained within the channels 54 and 56 and within the conical recess 59 and so as to connect the through channel to the channels 49 and 60.

Figure 6:
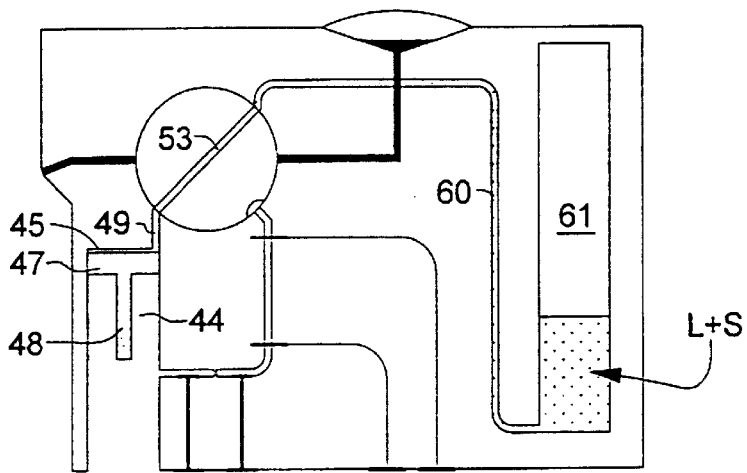
Figure 7:
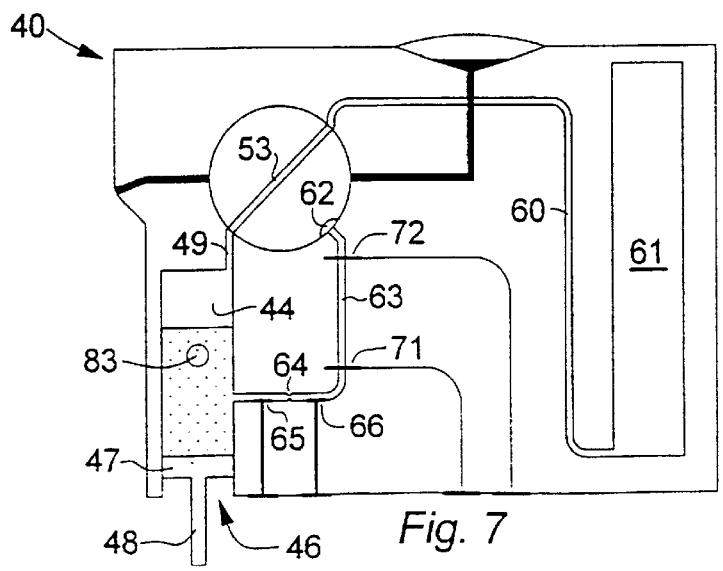

In the next step, shown in FIG. 6, the piston rod 48 is operated to displace the piston 47 towards the upper end 45 of the cylinder 44. Such displacement causes the liquid L to flow through the channel 49 into the through channel and displace the sample contained therein through the channel 60 into the space 61, where the major part of liquid L mixes with the sample brought along therewith. Only a minor part of the liquid L still remains within the channel 60 in an unmixed state. Air within the space 61, being originally under atmospheric pressure, is now compressed by the mixture of liquid L and sample S introduced therein.

Now, the piston rod is operated to displace the piston towards the lower end 46 of the cylinder as shown in FIG.

7. Such displacement causes the mixture of liquid L and sample S to be withdrawn from the space 61 through the channel 60, the through channel 53 and the channel 49 into the cylinder above the piston 47. Withdrawal is supported by the compressed air within the space 61 above the liquid level. When the piston passes its original position, the pressure within the cylinder 44 is restored to its original value. Further displacement of the piston towards the lower end 46 of the cylinder causes a negative pressure within the cylinder, and when the piston passes the mouth of the channel 63, communication is established between the cylinder and the bleed recess 62 through the capillary 64. Atmospheric air is now drawn into the cylinder 44, and the bubbles thereby created cause a further mixing of the liquid L and the sample S within the cylinder 44. The piston is kept in position until the pressure within the cylinder has been equalized.

Figure 8:
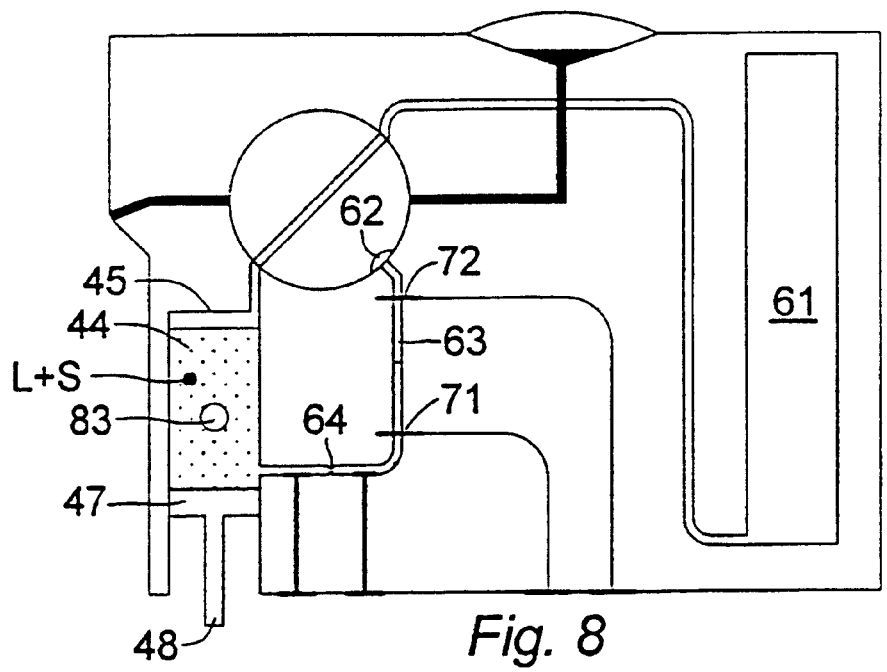
Figure 9:
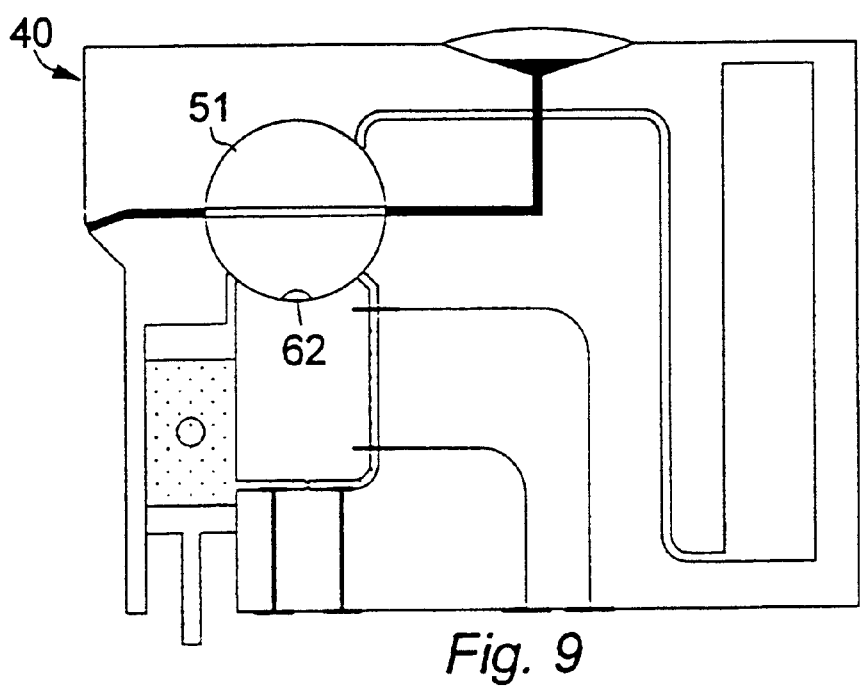
Figure 10:
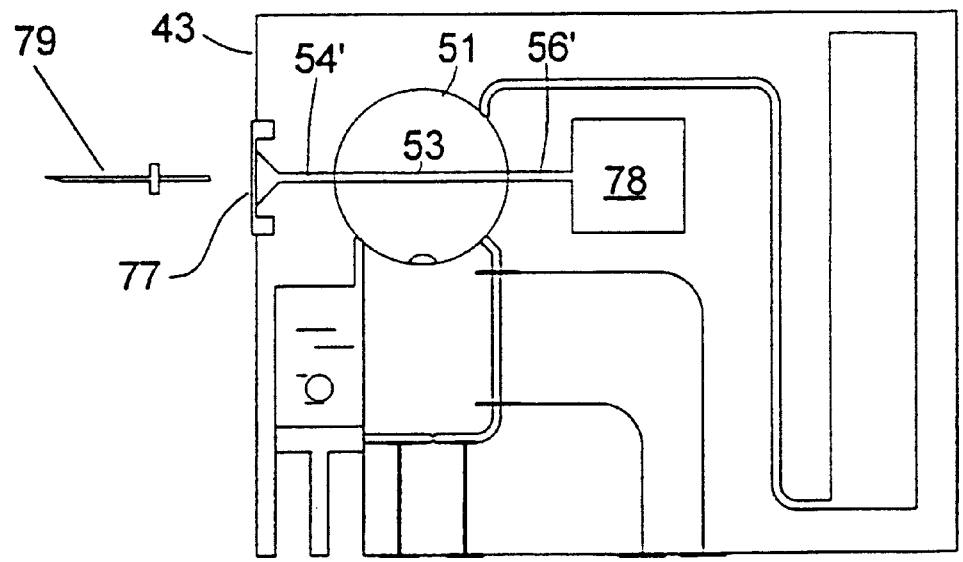
FIGS. 10 and 11 show corresponding sections through a second embodiment of the present invention.
Figure 11:
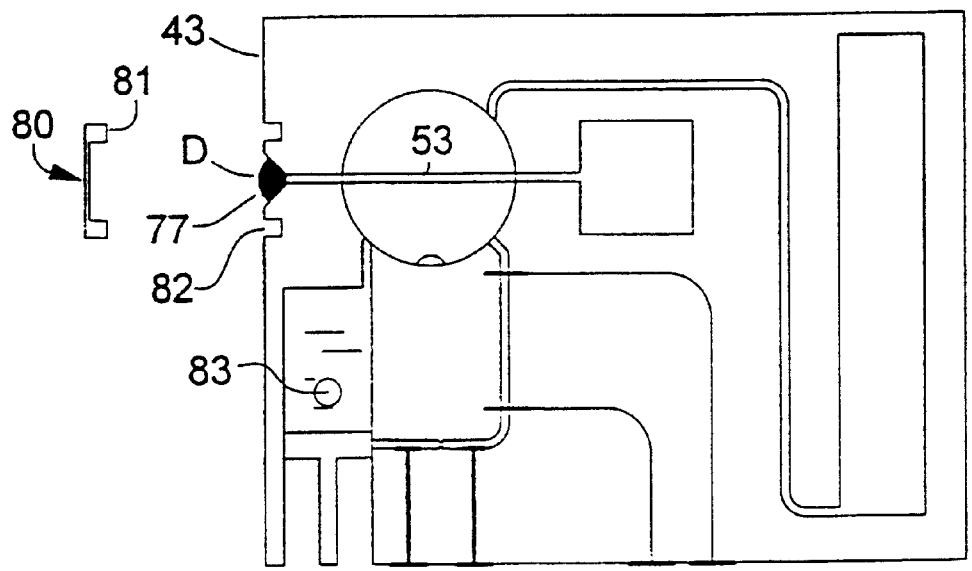

The piston rod 48 is then operated according to FIG. 8 to displace the piston 47 a relatively short distance towards the upper end 45 of the cylinder to create an overpressure within the cylinder 44 above the piston and within the space 61 thereby to displace at least a portion of the mixed and diluted sample L+S through the capillary 64 located in the channel 63. When the sample reaches the detector 71, counting is started, and when it reaches the detector 72, counting is stopped. In this position, or shortly thereafter, the valve body 51 is returned to its first position, shown in FIG. 9, such that the bleed recess 62 is closed. In this final position, the entire system is closed, and no waste liquid has to be disposed of since it is all contained within the housing 40.

second embodiment of the present invention shown in FIGS. 10 and 11 corresponds to the first embodiment in all respects except that there is no sucking means. Thus, all unchanged items bear the same reference numerals as in the first embodiment. Instead of sucking means there is provided in the front wall 43 a recessed aperture 77 having, e.g., a conical shape, and communicating through a channel 54' and the through channel 53 in the first position of the valve body 51 with a channel 56' leading to a closed space 78 containing atmospheric air.

The aperture 77 and the channel 54' are shaped so as to receive in a liquid tight manner a cannula 79 (FIG. 10) in cases where a blood sample is to be taken by way of venipuncture. In such case, the blood pressure within a vein is sufficient to press blood through at least the through channel 53 against the increasing air pressure within the space 78.

Alternatively, the second embodiment may be used for the finger-tip puncture (capillary) type of blood sampling. In that case, a drop of blood D is received within the aperture 77 (FIG. 11). In order to displace the sample through at least the through channel 53, there is provided a circular closure 80, also acting as a piston means, having an annular flange 81 mating with a corresponding annular recess 82 in the front wall 43. Placing the closure with its flange 81 in the recess 82, and further pressing the flange into the recess, will cause the drop of blood D to be displaced at least through the through channel 53. Thereafter, the closure may be sealed by an adhesive tape or the like. Alternatively, the flange 81 and the recess 82 may be made with co-operating interlocking snap-lock means permanently locking the closure and the housing once the closure is pressed into its bottom position.

Not mentioned before is a translucent light path 83 in the housing enabling photometric determination of certain parameters of the liquid contained in the cylinder 44, such as, initially, a reference value of the liquid L and the side walls of the body 40, and, finally, the haemoglobin value, e.g. in the position according to FIG. 8.

As initially stated, a device according to the present invention contains no electronic equipment necessary to perform the various measurements and calculations necessary.

Figure 12:
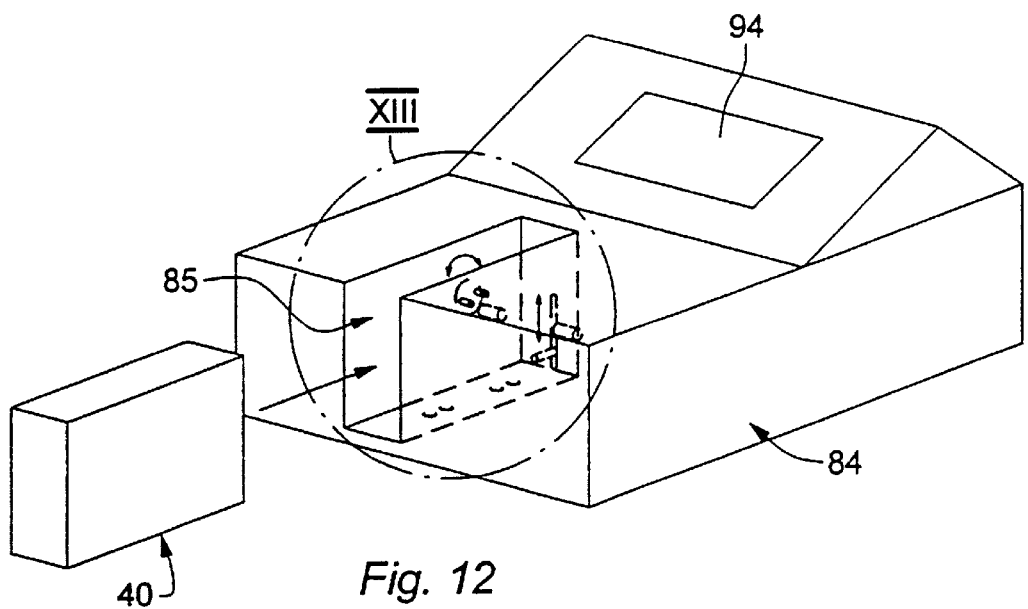
FIG. 12 shows a schematic perspective view of an embodiment of a particle counting apparatus and a disposable sampling device according to the present invention.
Figure 13:
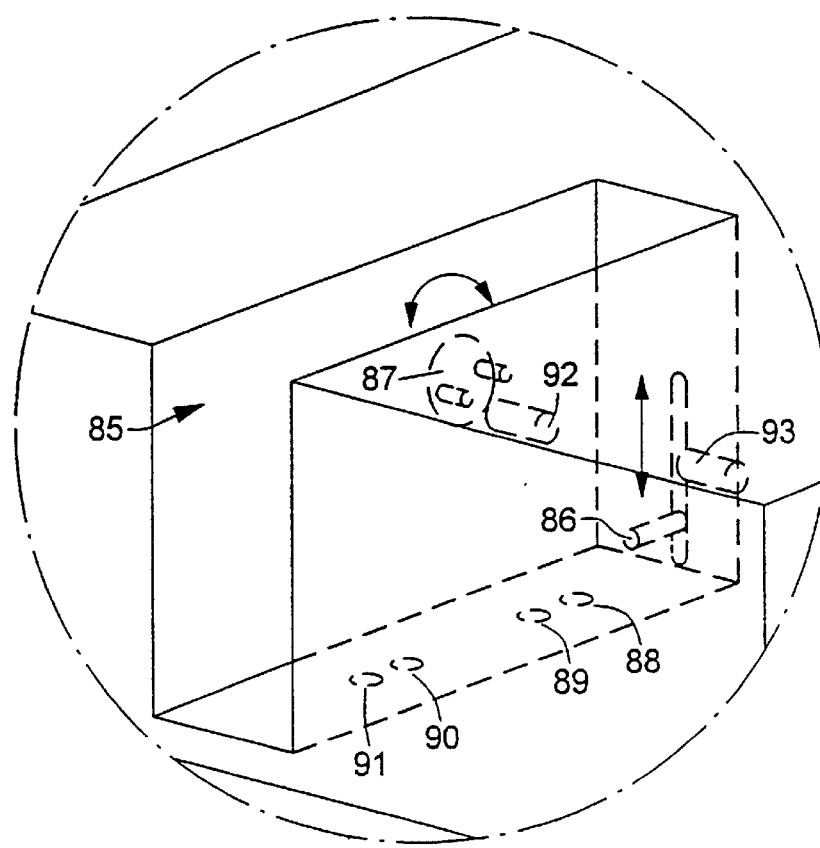
FIG. 13 shows the enlarged portion XIII of FIG. 12.

Instead, there is provided a counting apparatus 84 as exemplified in FIG. 12 for use as a base instrument for serving a plurality of disposable sampling devices according to the present invention. Such a base instrument can be placed, e.g., centrally Within a health care region to be used by several nurses acting in the field, or, centrally in a brewery. The counting apparatus 84 has means for receiving the housing 40 such as a slot 85. As best appears from the enlarged view of FIG. 13, there are operating means 86, 87 in the slot for cooperation with the piston rod 48 and the actuating means 51' for the valve body 51, respectively, terminal means 88, 89, and 90, 91 for cooperation with the terminals 69, 70, and 75, 76, respectively, as well as a light source 92 for sending a ray of light through the light path 83, and a light sensor 93 for photometric measurement through the cylinder 44.

When a disposable sampling device has been properly placed in the slot 85, the steps described with reference to FIGS. 5–9 can be automatically or manually initiated, and the result be displayed on a display 94.

Figure 14:
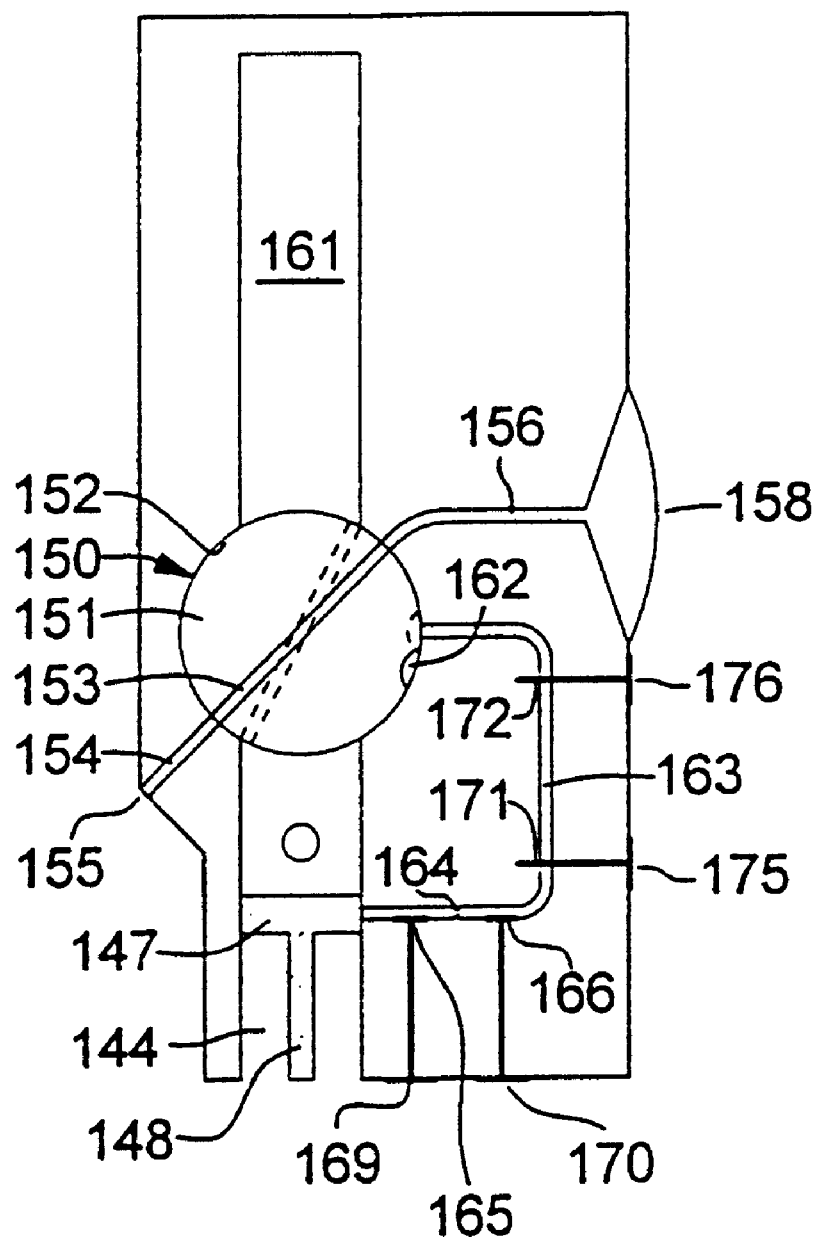
FIG. 14 shows a third embodiment of a disposable sampling device according to the present invention.

A preferred embodiment of a disposable sampling device according to the present invention, that is advantageous from a manufactural point of view, is shown in FIG. 14. Items corresponding to those of the first embodiment have the same reference numeral increased by 100. As appears, the cylinder 144 and the diluting chamber 161 are coaxially aligned and the valve chamber 150 is placed immediately therebetween such that its valve body 151 closes the opposed ends of the cylinder and the diluting chamber. In the first position of the valve body 151, corresponding to the position of the valve body 51 shown in FIGS. 2–4 and 9–11, its through channel 153 and bleed recess 162 are drawn in full lines, whereas the second position, corresponding to the position of the valve body 51 shown in FIGS. 5–8, is drawn in dotted lines. It appears that the angular distance between the two positions is considerably less than in the previous embodiment.

What is claimed is:

1. A disposable sampling device which connects to a separate apparatus for counting particles contained in a liquid collected into said sampling device, said device comprising:

a housing having therein:
- a.) a sample inlet in an outer wall of said housing;
- b.) means for introducing a sample from a source of said liquid into said sampling device through said inlet;
- c.) means for metering a defined volume of said sample connected to said introducing means;
- d.) a cylinder formed in said housing and having a piston movable there along, said piston having actuating means for imparting movement to said piston; wherein said cylinder and piston are connected to said metering means and dose a defined volume of a diluting liquid to said metering means for diluting said defined volume of sample located in the metering means;
- e.) a dilution chamber connectable to said metering means;
- f.) valve means comprising a valve chamber and a valve body for directing said defined volume of said sample and said defined volume of said diluting liquid located in said metering means to said dilution chamber; wherein said valve body is provided in said valve chamber and said metering means are provided in said valve body; said valve body being positionable in a first position connecting said sample inlet with said metering means, and in a second position connecting said cylinder through said metering means with said dilution chamber;

g.) conduit means formed within said housing interconnecting said sample inlet, said valve chamber, said cylinder and said dilution chamber;

h.) a measuring conduit formed in said housing connected to said cylinder and having particle detecting means therein; and i.) signal transmitting means connecting said particle detecting means with terminal means located in an outer wall of said housing.

2. The device according to claim 1, wherein said measuring conduit is closed by said piston in a first position of said piston.

3. The device according to claim 2, wherein said piston is operable in a first direction from said first position to a second position, in a second direction from said second position to said first position, in said second direction past said first position to a third position, and in said first direction from said third position to said first position.

4. The device according to claim 1, wherein said valve body includes means connecting said measuring conduit with atmosphere in said second position of said valve body.

5. The device according to claim 1, wherein a pump means is connected to said sample inlet in said first position of said valve body.

6. The device according to of claim 1, wherein said sample inlet is adapted to receive a cannula.

7. The device according to claim 1, wherein said sample inlet is sealable.

8. The device according to claim 1, wherein said valve chamber is cylindrical and said valve body is rotatable within said valve chamber.

9. The device according to claim 1, wherein said terminal means is connectable to said separate apparatus for transmitting signals from said particle detecting means thereto.

10. A method for diluting and detecting particles in a sample liquid contained in a disposable sampling device comprising the steps of:

moving a piston in a first direction from a first position to a second position to displace a defined volume of a diluting liquid contained in a cylinder through a metering means into a diluting chamber, said defined volume of said diluting liquid also delivering a defined volume of a sample contained in said metering means to said diluting chamber;

moving said piston in a second direction from said second position to said first position to withdraw a combined volume of said defined volume of sample diluted by said defined volume of diluting liquid from said diluting chamber to said cylinder;

further moving said piston in said second direction past said first position towards a third position, thereby opening a measuring conduit and causing air to be let into said cylinder therethrough; and moving said piston in said first direction from said third position to said first position, thereby expelling at least a portion of said combined volume through said measuring conduit past a particle detecting means.

11. A disposable sampling device for collecting a sample fluid containing particles to be counted comprising:

a housing having an outer wall with a sample inlet therein for applying a sample of fluid to the device; said housing having therein a metering means for collecting a defined volume of sample from the inlet;

a valve body for connecting said metering means to a cylinder;

a piston for dosing a defined volume of diluting liquid held within the cylinder into the metering means thereby forcing the defined volume of sample in the metering means to a dilution chamber for diluting the sample with the defined volume of diluting liquid; and a measuring conduit means connectable by said valve body to the cylinder upon the cylinder receiving a mixed volume of sample and diluting liquid from the dilution chamber.

* * * * *